United States Patent [19]

Hiai et al.

[11] Patent Number: 4,656,013
[45] Date of Patent: Apr. 7, 1987

[54] PROCESS FOR PRODUCING GERMANES

[75] Inventors: Athuhiko Hiai; Kazuo Wakimura; Masao Tanaka, all of Osaka, Japan

[73] Assignee: Mitsui Toatsu Chemicals, Inc., Japan

[21] Appl. No.: 786,568

[22] Filed: Oct. 11, 1985

[51] Int. Cl.$^4$ ............................................. C01G 17/00
[52] U.S. Cl. ...................................... 423/89; 423/645
[58] Field of Search ........................ 423/645, 89, 98; 75/121

[56] References Cited

PUBLICATIONS

Devyatykh, G. G., "Preparation of Germane by Treating Germanium Tetrachloride with Diisolbutylaluminum Hydrid" (U.S.S.R.) abstracted in Chem Abs vol. 76, 1972, 70761w.

Primary Examiner—John Doll
Assistant Examiner—Robert L. Stoll
Attorney, Agent, or Firm—Sughrue, Mion, Zinn, Macpeak, and Seas

[57] ABSTRACT

There is disclosed a process for producing germanes by reducing germanium halide with a mixture of alkylaluminum hydride and trialkylaluminum, in which a treatment for reducing the content of trialkylaluminum in the mixture to 10 mol. % or less relative to the alkylaluminum hydride is carried out prior to the reduction reaction. As to the treatment for reducing the content of trialkylaluminum in the mixture, there are provided, for example, distillation, recrystallization, complex formation followed by separation, pyrolysis and decomposition by hydrogenation and addition of alkylaluminum halide to said mixture.

1 Claim, No Drawings

PROCESS FOR PRODUCING GERMANES

BACKGROUND OF THE INVENTION

This invention relates to a process for the production of germanes such as monogermane, digermane and trigermane and particularly, to a process for the production of germanes by reducing germanium halides with use of a mixture of alkylaluminum hydride and trialkylaluminum.

Germanes or germanium hydrides are useful as a gas for the production of semiconductors and particularly, monogermane is valuable as a gas for doping.

For the production of germanes, there are known a process by reacting a magnesium-germanium alloy with an acid (J. of American Chemical Society, Vol. 46, p. 657 (1924)) and a process by reducing germanium oxide with sodium borohydride in an aqueous solution (J. of Inorg. Nuclear Chemistry, Vol. 4, pp 22–23 (1957)). However, in the former process, higher order germanes are by produced and a yield ratio of lower order germanes particularly, monogermane to the starting germanium is low (20% or less). Also, in the latter process, expensive sodium borohydride is used as a reducing agent as well as needing bromic acid as a reaction assistant and the selection of reaction conditions is difficult and further, the yield of end products is not satisfactory.

Furthermore, there is reported a process for the production of monogermane by reducing germanium tetrachloride with a reducing agent, for example, sodium borohydride and lithium aluminumhydride. This process, however, has disadvantages that the reducing agent is not only expensive, but the yield is not satisfactory (for example, J. of Chemical Society, pp 1984–1988 (1959)).

Also, there is known a process using sodium hydride relatively inexpensive as compared with the above-mentioned reducing agents. This process, however, needs using an expensive solvent such as diethyleneglycoldimethylether and adding a hydride soluble in said solvent such as sodium borohydride as a reduction assistant to the reaction system and accordingly, it is not convenient for industrial practice (Belgian Patent No. 890,356).

Furthermore, there is known a process for producing monogermane by reacting germanium tetrachloride with diisobutylaluminum hydride which is available in a commercial scale (Chemical Abstracts, Vol. 76, 20761W). According to this process, the yield is relatively good, but the resulting germanes have impurities such as other germanium hydrides than germanes and hydrocarbon compounds and accordingly, a large-scaled purification apparatus is necessary for use as the gas for semiconductors and thus, it is substantially impossible to carry out this process in a commercial scale.

On the other hand, as to alkylaluminum hydride it is difficult to industrially obtain it in pure form, but the alkylaluminum hydride is available easily and inexpensively in a commercial scale in the form of mixture with trialkylaluminum. Therefore, it is very valuable industrially if germanes can be effectively obtained by carrying out the reduction reaction with use of such a mixture of alkylaluminum hydride with trialkylaluminum.

The inventors have studied the reduction reaction of germanium halide using the above mixture and as a result, found that germanes obtained are very low in yield and monoethyl germanium ($GeH_3C_2H_5$) and monochlorogermanium ($GeH_3Cl$) are by-produced in large amount, probably by insufficient reduction of the germanium halide and also, ethane is formed in large amount, perhaps by side reactions.

SUMMARY OF THE INVENTION

An object of this invention is to provide a process for the production of germanes with a high yield and remarkably reduced by-products such as monochlorogermane and ethane by reducing germanium halide with a mixture of alkylaluminum hydride with trialkylaluminum which is available easily and inexpensively.

In accordance with this invention, there is provided a process for the production of germanes by reduction of germanium halide with alkylaluminum hydride which comprises preparing a mixture comprising an alkylaluminum hydride represented by Formula I, $$R_2^1AlH \qquad \text{I}$$

wherein $R_1$ is an alkyl group of 1 to 10 carbon atoms and the two alkyl groups may be the same or different and a trialkylaluminum represented by Formula II, $$R_3^2Al \qquad \text{II}$$

wherein $R_2$ is an alkyl group of 1 to 10 carbon atoms and the three alkyl groups may be the same or different, reducing the content of trialkylaluminum in said mixture to 10% by mole or less relative to the alkylaluminum hydride and carrying out a reduction reaction of the germanium halide with use of the thus obtained mixture containing mainly the alkylaluminum hydride.

DETAILED DESCRIPTION OF THE INVENTION

The germanium halides which may be used in this invention are represented by the general formula, $Ge_nX_{2n+2}$ wherein n is an integer of 1 to 5, preferably 1 to 3 and X is halogen atoms or hydrogen atom. Examples of the halogen atom are fluorine, chlorine, bromine and iodine. Particularly preferred germanium halides are tetrachlorogermanium (germanium tetrachloride), hexachlorodigermanium, trichlorogermanium, dichlorogermanium and monochloro- germanium.

According to this invention, first a mixture of alkylaluminum hydride with trialkylaluminum is prepared. In a commercial scale, such a mixture is easily available as intermediates in the step of producing alkylaluminum, for example by the steps of suspending aluminum powders in trialkylaluminum and adding hydrogen under elevated pressure.

Alkylaluminum hydride constituting the principal component in the reducing agent mixture is represented by the general formula I, $$R_2^1AlH \qquad \text{I}$$

wherein $R_1$ which may be the same or different is an alkyl group having 1 to 10 carbon atoms such as methyl, ethyl, n-propyl, iso-propyl, n-butyl, iso-butyl, sec-butyl, pentyl, hexyl, heptyl, octyl, nonyl or decyl. Among alkylaluminum hydrides represented by the formula I, particularly preferred examples include dimethylaluminum hydride, diethylaluminum hydride and diisobutylaluminum hydride. The alkyl groups of straight chain are preferred to those of side chain or branched chain. In case of using alkylaluminum hydrides having the side chain alkyl group, there is a tendency that the reaction products after reduction include comparative amount of germanium compounds by-produced in which halogen atoms of the germanium halide have been in part substituted by hydrogen, e.g. trihydrogermanium halide and that lower molecular weight hydrocarbon compounds such as methane, ethane, isobutane and isobutylene which are decomposition products resulting from dialkylaluminum hydride, are by-produced in comparative amount.

The trialkylaluminum present in the reducing agent mixture is represented by the general formula II, $$R_3{}^2Al \qquad \qquad II$$

wherein $R_2$ which may be the same or different is an alkyl group having 1 to 10 carbon atoms such as methyl, ethyl, n-propyl, iso-propyl, n-butyl, iso-butyl, sec-butyl, pentyl, hexyl, heptyl, octyl, nonyl or decyl. Among the trialkylaluminum compounds represented by the general formula II, those most frequently present in mixture with the alkylaluminum hydride are trimethylaluminum, triethylaluminum and triisobutylaluminum. Such a trialkylaluminum is present in said mixture usually in an amount of 20 to 300 mol. % to alkylaluminum hydride.

According to this invention, the mixture of alkylaluminum hydride with trialkylaluminum thus prepared is, next, treated to remove trialkylaluminum therefrom. The content of trialkylaluminum remaining after the treatment should be 10% by mole or less, preferably 8% or less, more preferably 6% or less relative to the alkylaluminum hydride. The lower limit of the content is not particularly set forth, though substantially 0% by mole is most preferred. If the remaining content of trialkylaluminum exceeds 10 mole % relative to alkylaluminum hydride, the yield of end products is remarkably reduced and ethane and halogenated germanium hydride are by-produced in large amount.

The treatment for removing the trialkylaluminum may be carried out by usually known unit operation or unit reaction, e.g. by distillation, recrystallization, complex formation followed by separation, pyrolysis of trialkylaluminum and decomposition by hydrogenation of trialkylaluminum.

Among such methods particularly preferred is the addition of an alkylaluminum halide capable of converting trialkylaluminum into dialkylaluminum monohalide to the reducing mixture.

Such alkylaluminum halides are represented by the general formula III, $$AlR_n{}^3X_{3-n} \qquad \qquad III$$

wherein $R_3$ stands for an alkyl having 1 to 10 carbon atoms, e.g. methyl, ethyl, n-propyl, iso-propyl, n-butyl, iso-butyl, sec-butyl, pentyl, hexyl, heptyl, octyl, nonyl or decyl, and X stands for a halogen atom such as fluorine, chlorine, bromine or iodine and n stands for a number 0, 1 or 1.5. In case n=0, the above-mentioned general formula represents aluminum trihalides not including alkyl radicals, for example aluminum trichloride.

Among the compounds represented by the general formula III, particularly preferred examples include methylaluminum dichloride, methylaluminum sesquichloride, ethylaluminum dichloride, ethylaluminum sesquichloride, isobutylaluminum dichloride, isobutylaluminum sesquichloride, aluminum trichloride, methylaluminum dibromide, methylaluminum sesquibromide, ethylaluminum dibromide, ethylaluminum sesquibromide, isobutylaluminum dibromide, isobutylaluminum sesquibromide and aluminum tribromide, which may be employed alone or in mixture.

The alkyl groups in alkylaluminum hydride and in trialkylaluminum present in said mixture and the alkyl groups in alkylaluminum halide to be added to said mixture may be all the same or different.

According to the present invention, the remaining content of trialkylaluminum in said mixture can be easily reduced to 10 mol. % or less relative to the alkylaluminum hydride by the addition of the alkylaluminum halide as explained above to said mixture, in such an amount enough for achieving such purpose. As for this amount of alkylaluminum halide to be added, the stoichiometrically required mole number calculated from the reaction equations as given below can be employed.

According to this invention, alkylaluminum di-, sesqui- and tri-halides react with trialkylaluminum to form dialkylaluminum monohalides as illustrated in the following reaction equations:

$$R_3Al + AlRX_2 \rightarrow 2AlR_2X \qquad \qquad IV$$

$$R_3Al + Al_2R_3X_3 \rightarrow 3AlR_2X \qquad \qquad V$$

$$2R_3Al + AlX_3 \rightarrow 3AlR_2X \qquad \qquad VI$$

As shown by the equations IV and V, alkylaluminum dihalide or alkylaluminum sesquihalide reacts in an equimolar ratio with trialkylaluminum to form alkylaluminum monohalide, but aluminum trihalide reacts, in half a molar amount as shown in the equation VI, with trialkylaluminum to form alkylaluminum monohalide.

In fact the above-mentioned reactions IV, V and VI may be considered to proceed in almost a stoichiometric manner, so that the amount of alkylaluminum halide to be added for decreasing the content of trialkylaluminum to 10 mol. % or less can be easily calculated from the initial content thereof relative to the alkylaluminum hydride present in the mixture. As an example, if the initial content of trialkylaluminum in the mixture is 200 mol. %, there may be added alkylaluminum halide in an amount enough for reacting at least 95% of trialkylaluminum present.

If the added amount of alkylaluminum halide is insufficient for decreasing the content of trialkylaluminum to 10 mol. % or less, there is scarcely achieved the object of this invention to significantly improve the yield of germanes and to significantly reduce by-products such as chlorogermanium, alkyl germanium and ethane or the like.

The addition of alkylaluminum halide to the reducing mixture may be conducted in an arbitrary manner, for example direct mixing of the two or mixing after either or both are diluted with a suitable solvent. Both components are usually liquid, but either component, if solid, may be dissolved or suspended in a solvent before mixing. Said mixing, being strongly exothermic in most cases, has to be carefully conducted in order to avoid overheating of the system. More specifically, it is preferable to charge either component in a container equipped with cooling and agitating means and to dropwise add the other under cooling and agitation and at a rate allowing temperature control thereby maintaining the temperature of the system at approximately 40° C. The aforementioned reactions, being generally very rapid, can be considered practically complete at the end of the addition, but reaction is preferably extended for 10 to 20 minutes for safety. In a suspended system, heating up to about 70° C. is preferable for accelerating the reaction.

It is to be noted that when the remaining content of trialkylaluminum in the mixture is lowered to 10 mol. % or lower relative to alkylaluminum hydride by the addition of alkylaluminum halide, dialkylaluminum monohalide resulting in the mixture need not be separated therefrom and may be conveniently used as it is in subsequent reduction reaction.

The mixture of alkylaluminum hydride with trialkylaluminum often contains metallic aluminum in the form of fine powders having a particle size of $100\mu$ or less in amount of 0.005 wt. % or more, frequently 0.5 to 2 wt. %, which results from unreacted portion of the metallic aluminum used as one of the materials for synthesis of alkylaluminum hydride.

In case of the metallic aluminum present in the mixture as mentioned above, it is preferred that the alkylaluminum halide for removing the trialkylaluminum is not so much added. Not exceeding about 1.8 times the stoichiometrical mole number required for converting all the trialkylaluminum present in the mixture to dialkylaluminum monohalide is preferred. If the added amount of alkylaluminum halide is too excess over the stoichiometrical mole, the decomposition of alkylaluminum hydride is promoted during the reduction reaction and accordingly, the yield of end germanes is often markedly reduced.

It is more preferred to remove aluminum fine powders preliminarily from said mixture to the extent of 0.1% by weight or less, preferably 0.01% by weight or less whereby the formation of by-products such as alkylgermanes is reduced. A process for removing aluminum powders includes, for example, distillation of the mixture of dialkylaluminum hydride and trialkylaluminum followed by separation of aluminum powders or separation by filtration.

In this invention, the reduction reaction on germanium halides includes all the reactions for producing germanes from germanium halides defined above.

Consequently the reduction reaction of this invention includes the following reaction:

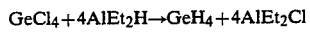

$$GeCl_4 + 4AlEt_2H \rightarrow GeH_4 + 4AlEt_2Cl$$

As for the ratio of germanium halide to dialkylaluminum hydride, it is preferred that the dialkylaluminum hydride is in excess of the stoichiometric ratio for forming germanes by substituting hydrogen atom for halogen atom, for example, 1.05–2.0 times the stoichiometric amount are preferred.

The reduction reaction can be conducted in known manner as a conventional liquid-to-liquid reaction, but it is to be noted that almost all the starting material, reducing agent and resulting substances are extremely active materials which are easily decomposed or generate fire by reaction with oxygen or moisture. Consequently the reaction has to be carried out in an inert atmosphere, completely free from oxygen and moisture. Thus the reaction system has to be completely sealed with an inert gas such as helium, neon, argon or xenon or a gas inactive to the reaction system such as nitrogen or hydrogen, which should be sufficiently deoxygenated and dried.

The reaction apparatus to be employed in the reduction reaction is preferably a conventional reactor for liquid-to-liquid reaction equipped with an agitator and a heat-eliminating means, and, because of the above-mentioned reason, has to be constructed as a completely closed system including the pipings attached thereto and the condenser for the resulting gaseous germanes.

The above-described apparatus for reduction reaction may also be used for adding and mixing alkylaluminum halide to the mixture of alkylaluminum hydride. It is therefore possible, in said apparatus, to at first effect the treatment of said mixture and then to conduct said reduction reaction by introducing germanium halides.

The reaction temperature in the process of this invention has to be maintained in a range from $-30°$ to $100°$ C., preferably from $0°$ to $80°$ C., most preferably from $30°$ to $50°$ C., since a lower reaction temperature is practically insufficient for the execution of the reaction, while a higher reaction temperature results not only in spontaneous decomposition of alkylaluminum hydride but also in undesired by-reactions.

The reduction reaction, being strongly exothermic, requires heating only at the start thereof. Once the reaction is initiated, the reaction proceeds automatically by the heat of reaction, and the reaction system is maintained at the desired reaction temperature by cooling. The reduction reaction may be conducted in a batch process in which the mixture of alkylaluminum hydride and germanium halide are both charged and reacted in the reaction, or in a semi-batch process in which either component, for example said mixture alone, is charged in the reactor while the other, for example germanium halide, is added thereto. The latter process has an advantage of controlling the reaction speed, and consequently the amount of heat of reaction, by the rate of addition of germanium halide. Naturally said reaction may also be conducted in continuous manner by continuously introducing the both components into the reactor and removing the reaction products also in continuous manner.

The reaction is usually conducted under a pressure ranging from atmospheric pressure to 2 $kg/cm^2$ (gage pressure), but may also be effected under a reduced or increased pressure in relation to the reaction temperature or reaction apparatus employed.

The reduction reaction, being very fast in nature, is considered practically complete when the mixing of both components is completed. Consequently, for example in the above-mentioned semi-batch process, the operation may be terminated if the reaction is continued for 10 to 30 minutes after the addition of germanium halide is completed. Also the end point of the reaction may be easily determined from the termination of generation of germanes or by the start of decline of measured temperature at the termination of exothermic reaction. Naturally the end point of the reaction can be most securely determined by the analysis of the composition of the reaction system or of the reaction products.

The generated germane gas is liquefied or solidified by introducing it into a condenser cooled with liquid nitrogen or the like and then collected.

In the reduction reaction in the process of this invention, the use of a reaction solvent is not essential but is generally preferable in view of decelerating the reaction and thus facilitating the control thereof.

The reaction solvent, if employed, is preferably a non-polar solvent not reacting with alkylaluminum monohalide nor forming a complex therewith in order to facilitate recovery of said alkylaluminum monohalide after the reduction reaction. Examples of such reaction solvent include aliphatic saturated hydrocarbons and aromatic hydrocarbons such as heptane, octane, liquid paraffin, benzene, toluene and xylene. Reactive solvents such as carbon tetrachloride are not usable in said reaction.

Certain polar solvents such as diethylether or tetrahydrofurane may be employed for accelerating the reaction at a lower temperature, but, in such case the separating operation becomes extremely difficult since such solvent forms a complex, which is not easily separable by a unit operation such as distillation, with alkylaluminum monohalide.

The germanes obtained by the process of this invention have little impurities and therefore, can be used as it is or after simple purification as materials for semiconductors.

EXAMPLE 1

A 500 ml stainless steel autoclave equipped with an induction stirrer was connected through a gas flow meter to a 500 ml stainless steel gas trap, and also connected to a constant rate pump for charging germanium tetrachloride dissolved in liquid paraffin through a dip tube. The entire system was filled with helium prior to the reaction, and the gas trap was cooled with liquid nitrogen.

A mixture of diethylaluminum hydride (60 wt. %) and triethylaluminum was distilled and diethylaluminum hydride containing triethylaluminum at a concentration of 2 mol. % was obtained.

35.3 g of said hydride was diluted in 50 g of liquid paraffin. The amounts of diethylaluminum hydride and triethylaluminum were 0.4 mols and 0.008 mols, respectively.

The obtained mixture was charged in the above-mentioned 500 ml autoclave, then degassed for 20 minutes under a pressure of 2 mmHg, and was maintained in helium atmosphere.

21.4 g (0.1 mols) of germanium tetrachloride dissolved in 28 g of liquid paraffin was supplied by the constant rate pump during 2 hours into the autoclave maintained at 50° C., and the generated gaseous germane was collected in the gas trap.

After the completion of the reaction, the gaseous germane remaining in the system was purged into the gas trap and collected therein by helium gas. The gas composition in the trap was measured by a gas chromatograph. The production of monogermane gas was 1.68 l under normal condition, corresponding to an yield of 75%.

The ratio of ethane produced to monogermane (ethane/GeH$_4$) was 0.53 vol. %, and the ratio of monochlorogermanium and monoethyl germanium to monogermane (GeH$_3$Cl+GeH$_3$C$_2$H$_5$/GeH$_4$) was 0.21 vol. %.

REFERENCE EXAMPLE 1

The process of the Example 1 was reproduced except that 57.2 g of the mixture before the separation by distillation, containing 0.4 mols of diethylaluminum hydride and 0.2 mols of triethylaluminum, was employed as the reducing agent. The production of monogermanium was 0.26 l under normal condition, corresponding to an yield of 12%.

The ratio of ethane/GeH$_4$ was 4.8%.
The ratio of GeH$_3$Cl+GeH$_3$C$_2$H$_5$/GeH$_4$ was 8.2%.

EXAMPLES 2, 3 AND REFERENCE EXAMPLES 2, 3

There was investigated the effect of triethylaluminum remaining in diethylaluminum hydride after the elimination of triethylaluminum by distillation from a mixture of the two.

The process and the apparatus were same as those in the Example 1.

The experimental conditions and results are summarized in Table 1.

The results shown in Table 1 indicate that the amount of triethylaluminum should be reduced to 10 mol. % or less relative to diethylaluminum hydride.

TABLE 1

| | AlEt$_3$ AlEt$_2$H (mol. %) | Yield (%) | Ethane GeH$_4$ (%) | GeH$_3$Cl + GeH$_3$C$_2$H$_5$ GeH$_4$ (%) |
|---|---|---|---|---|
| Example 2 | 6 | 75 | 0.32 | 0.32 |
| Example 3 | 10 | 74 | 0.48 | 0.47 |
| Reference Example 2 | 15 | 24 | 2.13 | 3.23 |
| Reference Example 3 | 25 | 13 | 6.32 | 8.50 |

EXAMPLE 4

569 g of a mixture of diethylaluminum hydride (43 wt. %), triethylaluminum and a small amount of tri-n-butyl aluminum was charged, with 42.3 g of powdered aluminum, in a 3 l stainless steel autoclave.

The mixture was agitated for 4 hours at 130° C. in an atmosphere of hydrogen at a pressure of ca. 140 kg/cm$^2$ (gage pressure).

After the reaction, the reaction mixture was filtered to obtain 539 g of a colorless transparent liquid, which contained 92.4 mol. % of diethylaluminum hydride, 6.3 mol. % of triethylaluminum and 1.3 mol. % of tri-n-butyl aluminum.

This mixture 41.5 g was employed in the synthesis of monogermane according to the conditions described in the Example 1 except that helium was replaced by hydrogen.

In this case the amount of diethylaluminum hydride employed was 0.44 moles.

The production of gaseous monogermane was 1.77 l under normal condition, corresponding to an yield of 79%.

The ratio of ethane produced to monogermane was 0.13 vol. %, and that of monochlorogermane +monoethyl germane to monogermane was 0.15 vol. %.

EXAMPLE 5

There was investigated the effect of elimination of trialkylaluminum by the addition of alkylaluminum halide.

The apparatus employed for the synthesis of monogermane was same as that described in the Example 1.

52.9 g of a mixture of diethylaluminum hydride (65 wt. %) and triethylaluminum (35 wt. %) was diluted with 50 g of liquid paraffin. In this case the amounts of diethylaluminum hydride and triethylaluminum were 0.4 moles and 0.162 moles, respectively. Consequently triethylaluminum existed at a concentration of 41 mol. % to diethylaluminum hydride.

To said mixture added dropwise is 20.6 g (0.162 moles) of ethylaluminum dichloride dissolved in 40 g of liquid paraffin. The amount of ethylaluminum dichloride corresponds to stoichiometric conversion of triethylaluminum in said mixture into diethylaluminum monochloride.

Thus, after the dissolving of the above-mentioned three alkylaluminum compounds, the ratio of triethylaluminum to diethylaluminum hydride was reduced to substantially 0 mol. %.

The mixture thus obtained was degassed at 30° C. under a reduced pressure of 2 mmHg for 20 minutes and then was charged into a 500 ml autoclave under an atmosphere of hydrogen.

21.4 g (0.1 moles) of germanium tetrachloride dissolved in 28 g of liquid paraffin was charged from a constant rate pump over 2 hours into the autoclave maintained at 45° C. The generated monogermane gas was collected in the gas trap.

After the reaction was complete, the monogermane gas remaining in the reaction system was purged with hydrogen gas into the gas trap.

The composition of the trapped gas was determined with a gas chromatograph.

The production of monogermane gas was 1.90 l under normal condition, corresponding to an yield of 80%.

The ratio of ethane produced to monogermane (ethane/GeH$_4$) was 0.16 vol. %, and that of monochlorogermane and monoethylgermane to monogermane (GeH$_3$Cl+GeH$_3$C$_2$H$_5$/GeH$_4$) was 0.12 vol. %.

EXAMPLE 6

The treatment of the reducing agent was carried out in the same manner as in Example 5 and hexachlorogermanium was fed as the germanium material. The feed amount of hexachlorogermanium was 35.7 g (0.1 mole). The yield of digermane, from the gas composition in the trap measured by a gas chromatograph, was calculated as 65%.

The production amount of ethane to monogermane was 0.2 vol. %. Unreduced chlorine compounds could not be identified.

EXAMPLE 7

A 500 ml stainless steel autoclave equipped with an induction stirrer and an oil bath for controlling of temperature was connected with a 500 ml stainless steel gas trap through a gas flow meter. Also, the autoclave was connected with a constant rate pump for charging germanium tetrachloride. The entire system was filled with helium prior to the reaction and the gas trap was cooled with liquid nitrogen.

To 100 g of a mixture of 60 wt. % of diethylaluminum hydride, 20% of triethylaluminum, 0.8% of aluminum fine powders and 19.2% of liquid paraffin (the mole % of triethylaluminum to alkylaluminum hydride in the mixture =25.1%) was added 21.1 g (0.166 moles) of ethylaluminum dichloride dissolved in 25 g of liquid paraffin, which was 95% of the stoichiometric mole and was such an amount that the remaining amount of triethylaluminum in said mixture was reduced to 1.25 mol. % relative to the diethylaluminum hydride.

37.3 g (0.174 moles) of germanium tetrachloride dissolved in 20 g of liquid paraffin were fed to the autoclave maintained at 40° C. with a constant rate pump over two hours and reduction reaction was carried out. Monogermane gas generated was collected in the trap. At the time the generation of gas almost discontinued, the remaining monogermane gas in the reaction system was purged with helium and fed to and collected in the trap. The composition of the trapped gas was measured by a gas chromatograph: Monogermane 3.20 Nl, Yield 82%.

EXAMPLE 8

The same procedure as in Example 7 was carried out except adding 14.2 g (0.112 moles) of ethylaluminum dichloride dissolved in 20 g of liquid paraffin. This addition amount was 64.1% of the stoichiometric mole and was such an amount that the remaining amount of triethylaluminum in the mixture was reduced to 9 mol. % relative to diethylaluminum hydride.

The amount of monogermane formed was 3.31 Nl and the yield was 85%.

EXAMPLE 9

The same apparatus as in Example 7 was used. To 100 g of a mixture of 50% of diethylaluminum hydride, 17% of triethylaluminum, 1.0% of aluminum fine powders and 32% of liquid paraffin (the mole % of triethylaluminum to diethylaluminum hydride in the mixture =25.6%) were added 32.1 g (0.253 moles) of ethylaluminum dichloride dissolved in 30 g of liquid paraffin, which was 1.7 times the stoichiometric mol.

Thereafter, 31.1 g (0.145 moles) of GeCl$_4$ dissolved in 15 g of liquid paraffin were fed in the same manner as in Example 7. The collected monogermane was 2.70 Nl and the yield was 83%.

REFERENCE EXAMPLE 4

The same procedure as in Example 9 was carried out except adding 7.85 g (0.0618 moles) of ethylaluminum dichloride dissolved in 10 g of liquid paraffin. This addition amount was 41.5% of the stoichiometric mole and was such an amount that the remaining amount of triethylaluminum in the mixture was reduced to 15 mol. % relative to diethylaluminum hydride.

The amount of monogermane formed was 1.14 Nl and the yield was 35%.

REFERENCE EXAMPLE 5

The same procedure as in Example 9 was carried out except adding 37.8 g (0.298 moles) of ethylaluminum dichloride dissolved in 30 g of liquid paraffin. This addition amount was 2.0 times the stoichiometric mole.

The amount of monogermane formed was 0.94 Nl and the yield was 29%.

EXAMPLES 10, 11 AND REFERENCE EXAMPLE 6

A 500 ml stainless steel autoclave equipped with induction stirrer was connected through a gas flow meter to a 500 ml stainless steel gas trap, and also connected to a constant rate pump for charging germanium tetrachloride dissolved in liquid paraffin through a dip tube. The entire system was filled with helium prior to the reaction, and the gas trap was cooled with liquid nitrogen.

A mixture of 70 wt. % of diethylaluminum hydride and 30 wt. % of triethylaluminum was prepared. As for Ref. Example 6, the mixture containing further 1.0 wt. % of aluminum powders based on the diethylaluminum hydride was used. As for Example 10, the mixture having aluminum powders removed to the extent of 0.008% by means of a pressurized filter precoated with diatom earth was used and as for Example 11, the mixture having aluminum powders removed to the extent of 0.0003% by means of single distillation thereby obtaining fractions up to 158° C. under reduced pressure of 11 mmHg was used. 49.2 g of each of these mixtures containing diethylaluminum hydride, triethylaluminum and aluminum powders were diluted with 50 g of liquid paraffin, wherein the amounts of diethylaluminum hydride and triethylaluminum were 0.4 moles and 0.129 moles, respectively.

To said mixture added dropwise were 16.4 g (0.129 moles) of ethylaluminum dichloride dissolved in 23 g of liquid paraffin. The amount of the ethylaluminum dichloride corresponds to stoichiometric conversion of triethylaluminum in said mixture into diethylaluminum monochloride. Each of the three mixtures thus obtained was degassed at 30° C. under a reduced pressure of 2 mmHg for 20 minutes and then was charged into a 500 ml autoclave under an atmosphere of helium. 21.4 g (0.1 moles) of germanium tetrachloride dissolved in 28 g of liquid paraffin was charged from a constant rate pump over 2 hours into the autoclave maintained at 40° C. The generated monogermane gas was collected in the gas trap. After the reaction was complete, the monogermane gas remaining in the reaction system was purged with helium gas into the gas trap.

The composition of the trapped gas was determined with a gas chromatograph.

The results obtained are set forth in Table 2.

TABLE 2

|  | $GeH_4/GeCl_4$ mol % | $GeH_3C_2H_5 + GeH_3Cl/GeCl_4$ mol % |
|---|---|---|
| Example 10 | 81.6 | 5.4 |
| Example 11 | 86.2 | 3.9 |
| Ref. Ex. 6 | 75.3 | 12.8 |

What is claimed is:

1. In a process for the production of germanes by reduction of germanium halide with alkylaluminum hydride, the improvement which comprises using as said alkylaluminum hydride a mixture comprising an alkylaluminum hydride represented by Formula I.

$$R_2^1AlH \qquad \qquad I$$

wherein $R^1$ is an alkyl group of 1 to 10 carbon atoms and the two alkyl groups may be the same or different and 20 to 300 mol % relative to the alkylaluminum hydride of a trialkylaluminum represented by Formula II, $$R_3^2Al \qquad \qquad II$$

wherein $R^2$ is an alkyl group of 1 to 10 carbon atoms and the three alkyl groups may be the same or different, to which mixture an amount of alkylaluminum halide represented by the general Formula III, $$AlR_n^3X_{3-n} \qquad \qquad III$$

wherein $R^3$ is an alkyl group having 1 to 10 carbon atoms, n is a number equal to 0, 1 or 1.5 and X is a halogen atom has been added in an amount sufficient to reduce the content of trialkylaluminum in said mixture to 10 mol % or less relative to the alkylaluminum hydride by converting trialkylaluminum to dialkylaluminum monohalide, said mixture containing the dialkylaluminum monohalide being used for the reduction reaction without separating the dialkylaluminum monohalide from said mixture.

* * * * *